(12) United States Patent
Taylor

(10) Patent No.: US 6,942,701 B2
(45) Date of Patent: Sep. 13, 2005

(54) PROSTHESIS

(75) Inventor: Andrew Clive Taylor, Nr. Chichester (GB)

(73) Assignee: Finsbury (Development) Limited, Leatherhead (GB)

( * ) Notice: Subject to any disclaimer, the term of this patent is extended or adjusted under 35 U.S.C. 154(b) by 0 days.

(21) Appl. No.: 10/271,624

(22) Filed: Oct. 16, 2002

(65) Prior Publication Data
US 2003/0074077 A1 Apr. 17, 2003

(30) Foreign Application Priority Data
Oct. 16, 2001 (GB) ............................................. 0124847

(51) Int. Cl.⁷ ................................................. A61F 2/36
(52) U.S. Cl. ................................... 623/22.14; 623/22.3
(58) Field of Search ........................... 623/22.21, 22.26, 623/22.3, 22.24, 23.41, 23.17, 23.32, 22.14

(56) References Cited

U.S. PATENT DOCUMENTS

| | | | |
|---|---|---|---|
| 4,718,914 A | | 1/1988 | Frey et al. |
| 5,080,678 A | * | 1/1992 | Spotorno et al. ............. 623/22 |
| 5,201,881 A | | 4/1993 | Evans |
| 5,549,697 A | * | 8/1996 | Caldarise .................... 623/22 |
| 6,059,833 A | * | 5/2000 | Doets ......................... 623/22 |
| 6,132,469 A | | 10/2000 | Schroeder |

FOREIGN PATENT DOCUMENTS

| | | | |
|---|---|---|---|
| EP | 0066092 A1 | * | 4/1982 |
| EP | 1 066 806 A1 | | 1/2001 |

OTHER PUBLICATIONS

European Search Report, EP 02 25 7153, dated Dec. 16, 2003, 3 pages.

* cited by examiner

*Primary Examiner*—Bruce Snow
(74) *Attorney, Agent, or Firm*—Senniger Powers

(57) ABSTRACT

The invention provides an acetabular prosthesis comprising an outer portion having a substantally concave inner surface and a substantially convex outer surface. An inner portion within and spaced from the outer portion and having a substantially concave inner surface defining a cavity and a substantially convex outer surface. Flexible connecting means, such as vanes, connect the outer convex surface of the inner portion to the concave inner surface of the outer portion. Such an acetabular prosthesis can exhibit matched compliance between the outer portion and the patient's pelvis while the inner portion accommodates idealised rigidity for artificial articulation components.

19 Claims, 8 Drawing Sheets

PROSTHESIS

BACKGROUND OF THE INVENTION

This invention relates to an acetabular prosthesis.

It is well known that a major factor influencing the life expectancy of a prosthetic implant is fatigue fracture and wear. Frictionally induced torque stresses acting through the prosthesis can result in the breakage of either the bone or the cement used to bond the prosthesis to the bone. For example, the pressure placed on an acetabular implant during the course of normal movement can be as high as several tonnes/cm$^2$. Such loads may lead to a very high risk of failure of the implant. If a breakage of the hip bone or cement occurs, wear is inevitable. This can lead to particle formation which causes osteolysis and adverse tissue reactions. These factors not only reduce the life expectancy of a prosthesis but can cause considerable damage to the bone of the patient.

Currently the life expectancy of an acetabular prosthesis is typically about ten years. If the prosthesis is to be implanted into an elderly patient then such a working life span is not problematic as the prosthesis might reasonably be expected to function for the lifetime of the patient. However, when such a prosthesis is implanted into a young patient, it is likely that one or more revision operations will have to be performed during the lifetime of the patient. It is highly undesirable to subject patients repeatedly to the trauma of such a major surgical procedure as is required to replace a failed prosthesis.

SUMMARY OF THE INVENTION

There is a need in the art to provide an acetabular prosthesis which is capable of applying load distribution to a hip joint in a manner which mimics that of a natural hip joint and thereby promotes healthy bone generation and regeneration, thus maximising the life expectancy of the prosthesis and reducing the likelihood of further surgery for replacement or repair being required.

According to the present invention there is provided an acetabular prosthesis comprising:

an outer portion having a substantially concave inner surface and a substantially convex outer surface;

an inner portion within and spaced from the outer portion and having a substantially concave inner surface defining a cavity and a substantially convex outer surface; and flexible connecting means connecting the outer convex surface of the inner portion to the concave inner surface of the outer portion.

The acetabular prosthesis of the invention is preferably made from a biocompatible material, such as a titanium alloy or cobalt-chrome. Preferably, however, it is formed at least in part from a material possessing typical characteristics of heterogeneity and anisotropy such as a carbon fibre-reinforced plastics material or similar compliant material. Hence at least a part selected from the flexible connecting means, the outer portion, and the inner portion may be made from a titanium alloy, from cobalt chrome, or from a carbon fibre-reinforced plastics material, for example a carbon fibre-reinforced epoxy resin material.

If the prosthesis is made using a carbon fibre-reinforced resin material, the compliance can be tailored throughout the implant so that this possesses an appropriate stiffness throughout. Thus the use of a carbon fibre-reinforced resin material allows the stiffness to be changed in any direction at any point in the prosthesis.

Although when a carbon fibre-reinforced plastics material is used the inner concave surface of the cavity of the inner portion can be suitably coated to provide a part spherical bearing surface for the ball head of a femoral prosthesis, it will normally be more practical to provide a polished concave part spherical bearing surface for the ball head of a femoral prosthesis on a metal insert which is snugly received in the cavity or to provide a ceramic liner or a plastics material liner having in either case a part spherical bearing surface which is snugly received in the cavity. Typically a ball head on a femoral prosthesis has a nominal diameter of 25 mm. Hence the acetabular prosthesis according to the invention is preferably adapted so that a metal, plastics, or ceramic insert having a concave part spherical bearing surface may be snugly received in the cavity. Such an insert may be retained in place in the cavity by adhesive bonding or by a press-fit or snap locking arrangement. Alternatively the inner portion may be moulded around the insert so as to prevent removal of the insert therefrom.

In one particularly preferred embodiment of the invention the cavity is defined in part by a substantially frusto-conical surface. Alternatively the cavity can be defined by a substantially part spherical concave inner surface. In this case the inner portion may be made from a titanium alloy or cobalt-chrome, while the substantially part spherical concave inner surface may be provided with a polished finish.

In a particularly preferred form of acetabular prosthesis, the flexible connecting means comprises a plurality of petaloid vanes, for example three petaloid vanes, integrally formed with the inner and outer portions. Usually it will be preferred for the vanes to join the outer surface of the inner portion and the inner surface of the outer portion in each case along spiral paths.

If desired, at least a part, and preferably all, of the space remaining between the inner portion and the outer portion can be filled with a resilient material, such as a silicone rubber.

The acetabular prosthesis of the invention is designed for implantation into a surgically prepared cavity in the hip of a patient. Since the human pelvis comprises a structure of three bones with considerable flexibility, a normal pelvis can accommodate reasonable stresses and deformation imposed, for example, by vigorous exercise or by leaping off a fence, by relative movement between these bones. Moreover the pelvic bones themselves can flex considerably to accommodate such loading. On the other hand a conventional acetabular prosthesis, which is typically made of titanium, a titanium alloy or cobalt-chrome, is much more rigid than the surrounding bone in which it is implanted. Normally such conventional acetabular prostheses will be held in place by engagement of exterior screw threads positioned substantially equatorially around the periphery of the prosthesis with the patient's bone, by means of screws, by means of bone cement, or by a combination of these. Because a conventional implant is much more rigid than the patient's bone, there is a considerable risk of damage occurring when a patient's hip in which the acetabular prosthesis has been implanted is subjected to stress. This damage can manifest itself in damage to the pelvic bones, in fracture of the bond between the prosthesis and the surrounding bone, or in progressive migration of the implant leading to failure. If the damage is sufficiently severe, then a revision operation may be necessary.

The acetabular prosthesis of the present invention may be secured in place by use of external screw threads, by use of screws, by use of bone cement, or by a combination of two or more of these methods of securement; alternatively, or in addition to one or more of these methods of securement, the substantially convex outer surface of the outer portion of the acetabular prosthesis of the present invention may be formed at least in part as a porous surface or provided with an adhesively bonded bone promotion layer, such as a layer of hydroxyapatite, so as to facilitate and promote bone ingrowth into the outer portion of the acetabular prosthesis.

Preferably the outer portion of the acetabular prosthesis of the invention is relatively flexible. Desirably its flexibility should match as closely as possible that of a typical human pelvic bone as a complete structure. In this way it can, after implantation in a patient, accommodate a localised increase in stress by absorbing stress applied to the hip joint as the patient undertakes his or her normal activities with a significantly reduced risk of any fracture of the bone or of the prosthesis becoming dislodged due, for example, to rupture of any cement bond by means of which the implant is retained in the bone.

BRIEF DESCRIPTION OF THE DRAWINGS

The inner portion of the cup is seated within the outer portion in such a way that a space is defined between at least a part of the concave surface of the outer portion and at least a part of the convex surface of the inner portion. This annular space provides a "flex zone" within which the inner portion can make localised movements relative to the flexible outer portion, as permitted by the flexibility of the connecting means. Thus the outer portion matches the ideal flexibility for pelvic compliance and the inner portion can optimise the rigidity required for ideal articulation of the replaced joint.

BRIEF DESCRIPTION OF THE DRAWINGS

Figure 1:
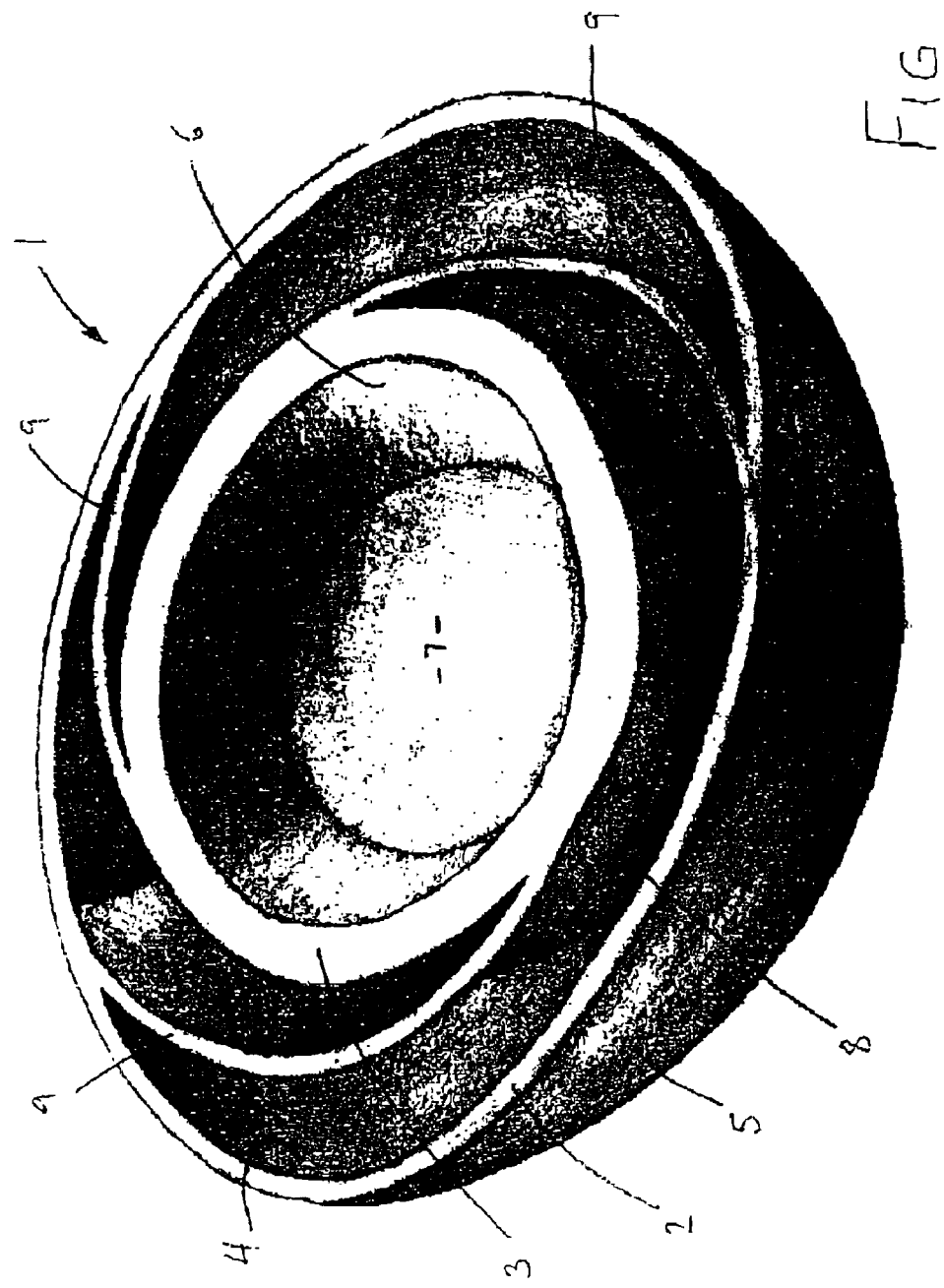
Figure 2:
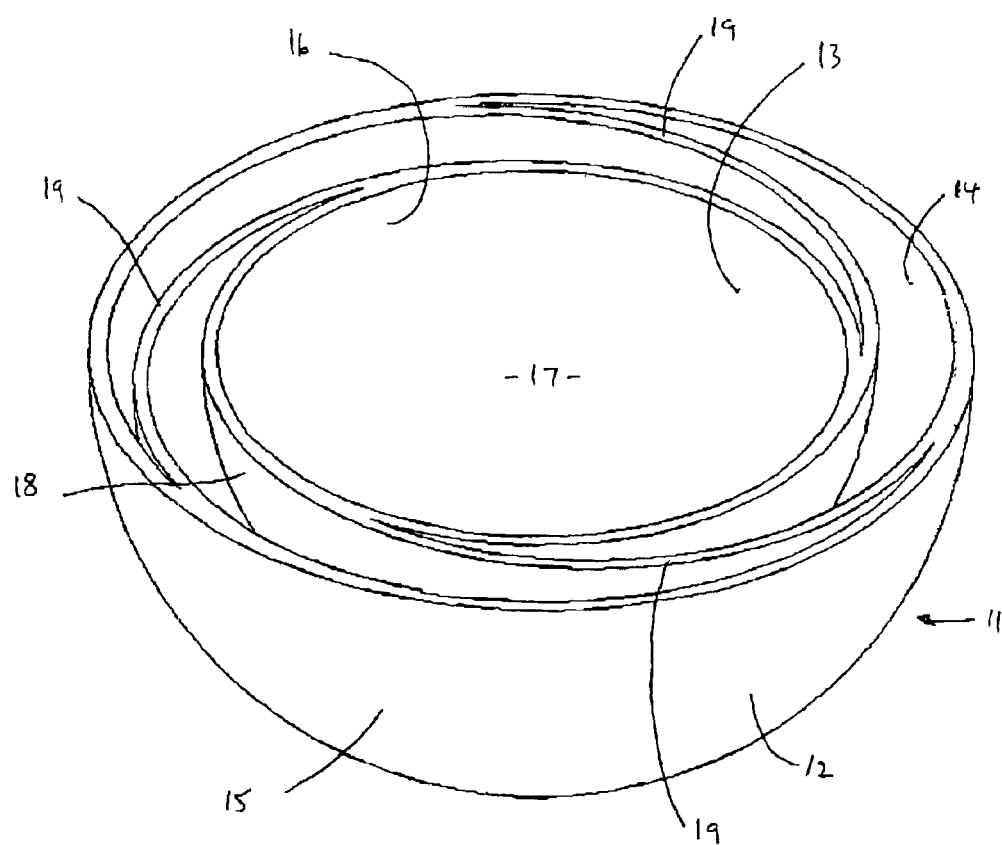
Figure 3:
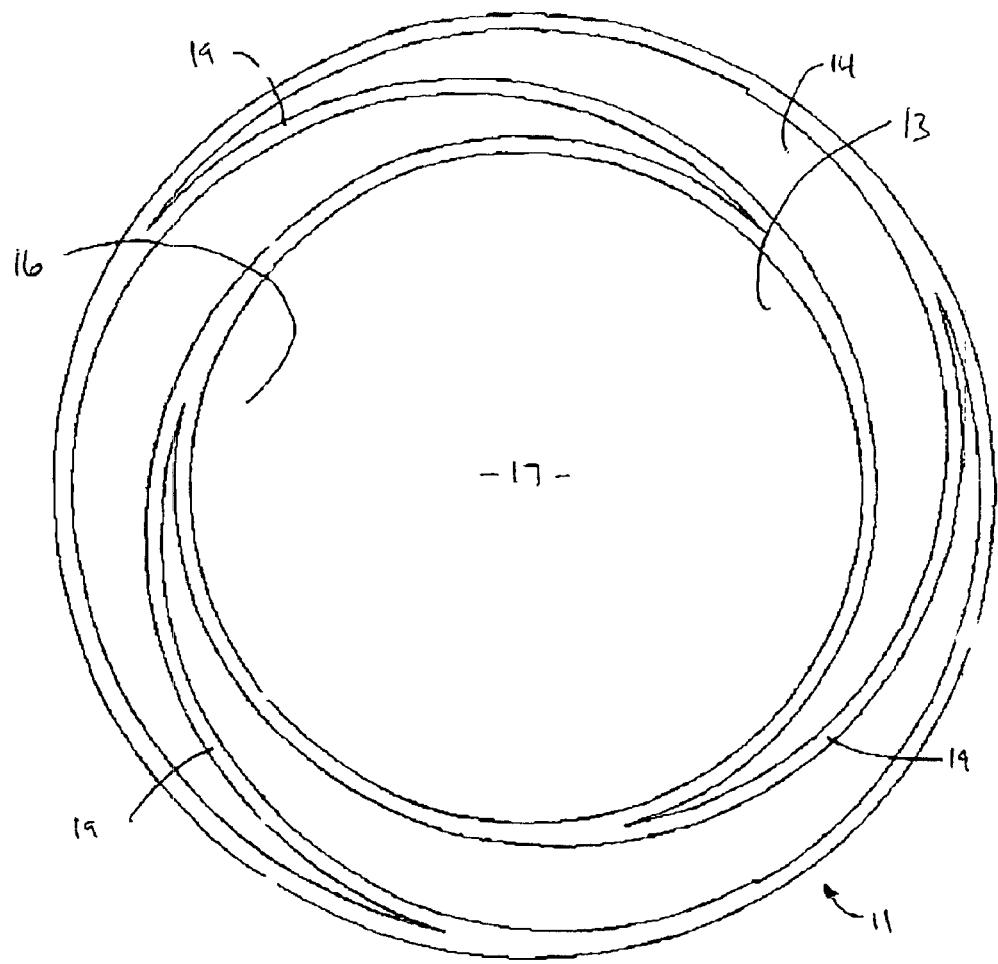
Figure 4:
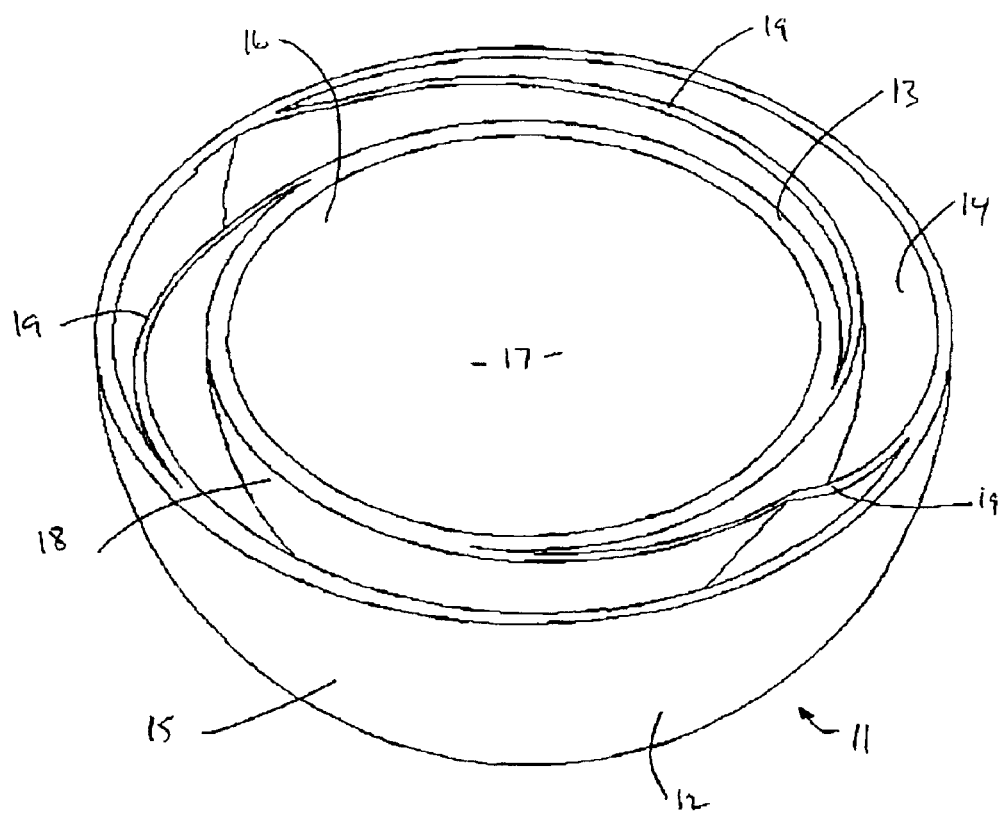
Figure 5:
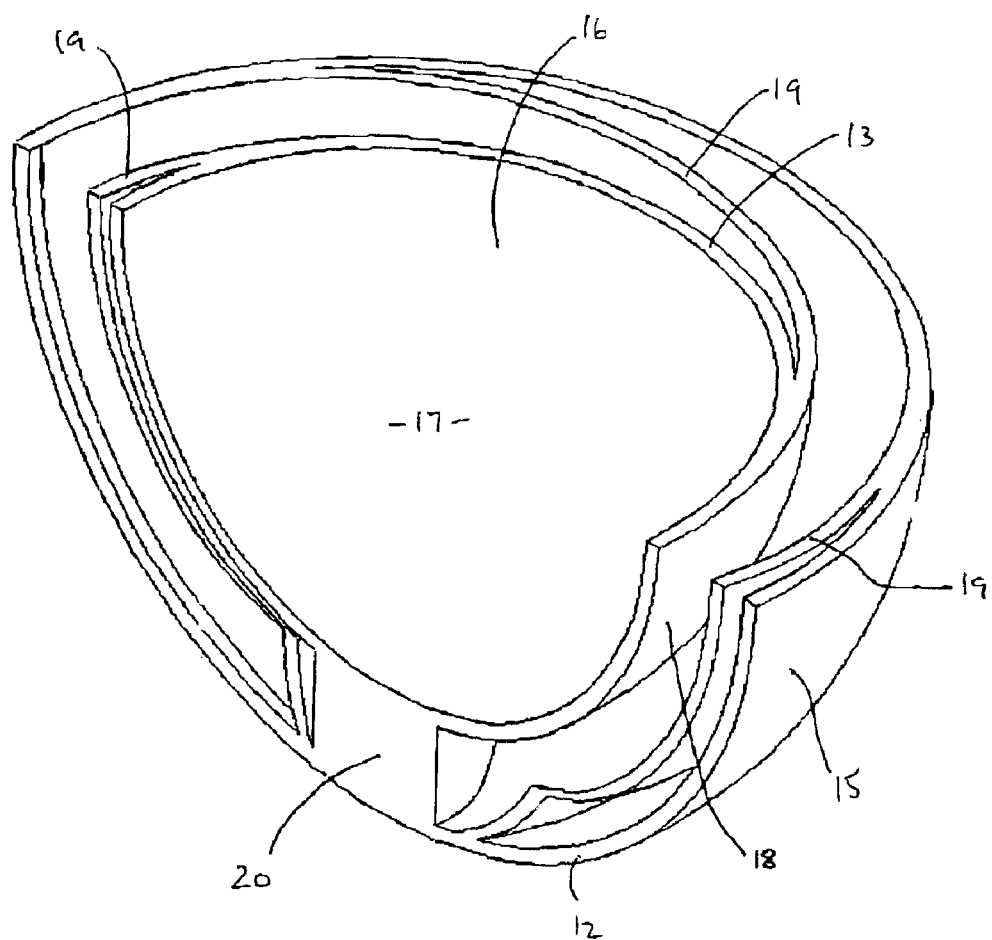

In order that the invention maybe clearly understood and readily carried into effect, some preferred embodiments thereof will now be described, by way of example only, with reference to the accompanying diagrammatic drawings, wherein:

FIG. 1 is a perspective view of an acetabular prosthesis constructed according to the invention;

FIG. 2 is a perspective view of a second acetabular prosthesis according to the invention;

FIG. 3 is a top plan view of the prosthesis of FIG. 2;

FIG. 4 is a first sectional view of the prosthesis of FIGS. 2 and 3;

FIG. 5 is a vertical section through the prosthesis of FIGS. 2 to 4; and

Figure 6:
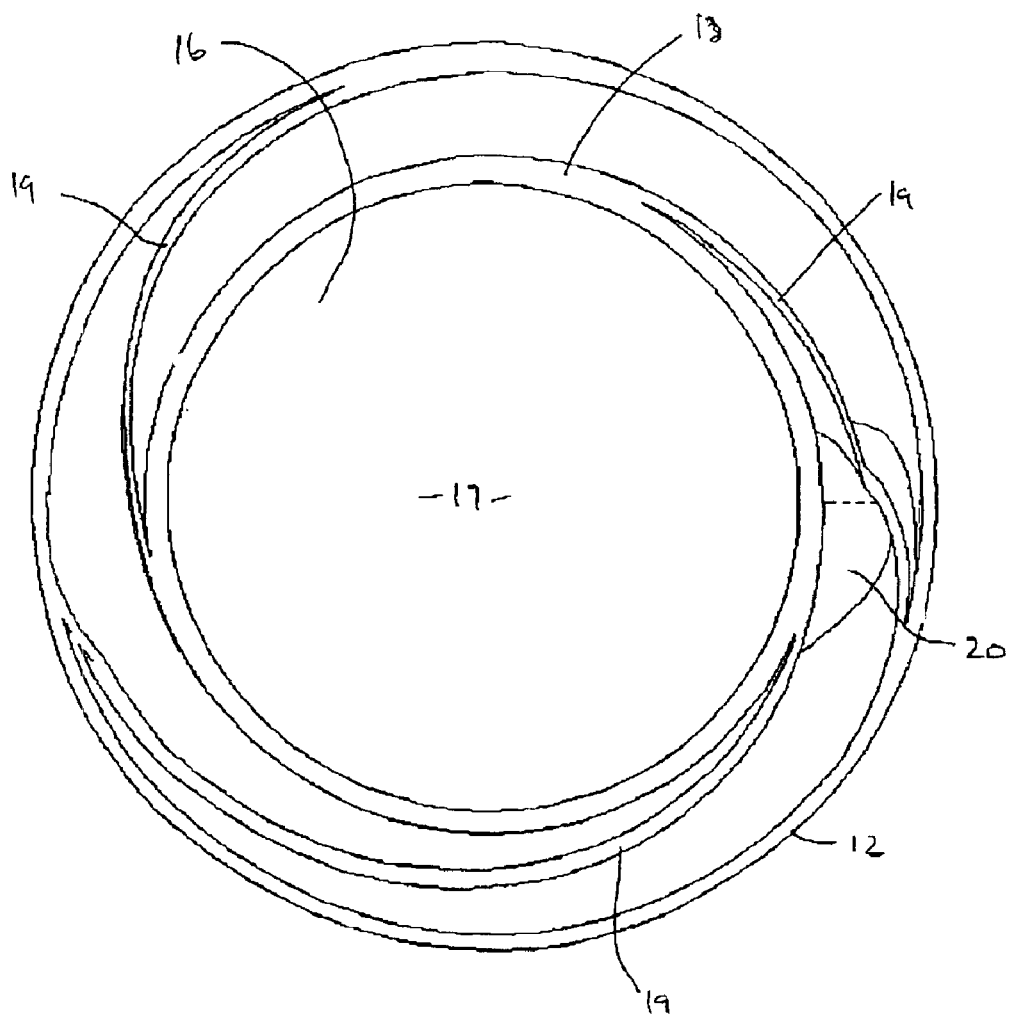
Figure 7:
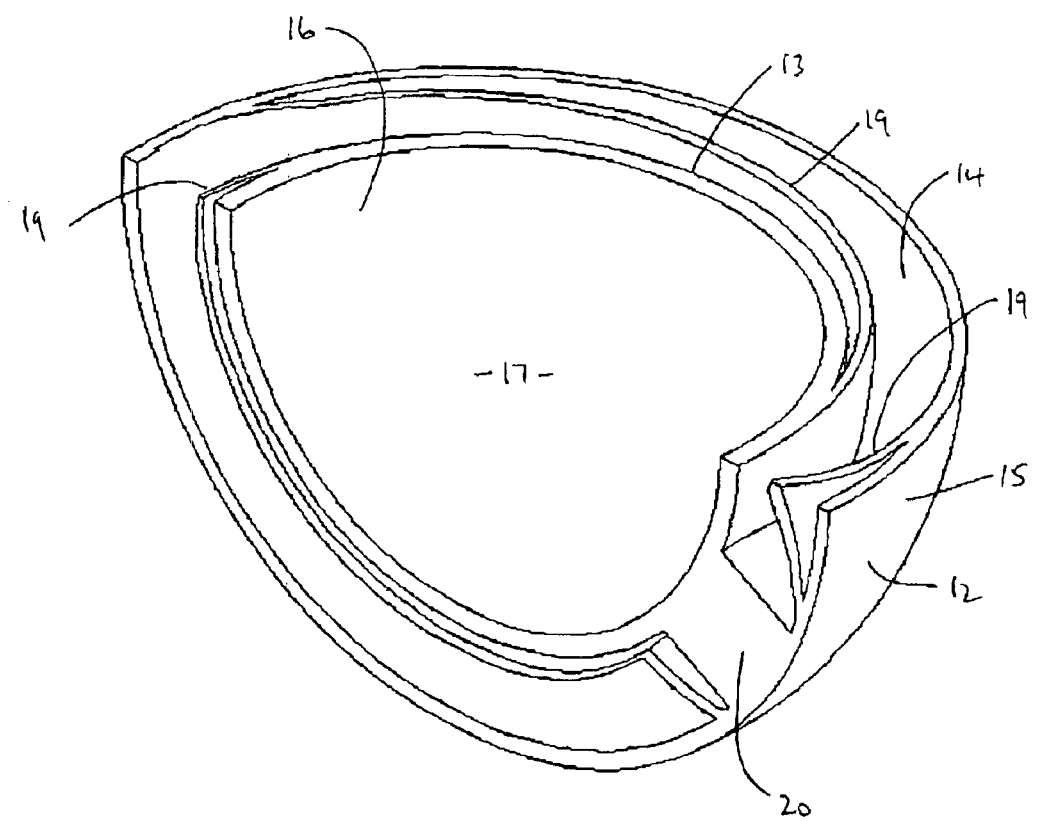
Figure 8:
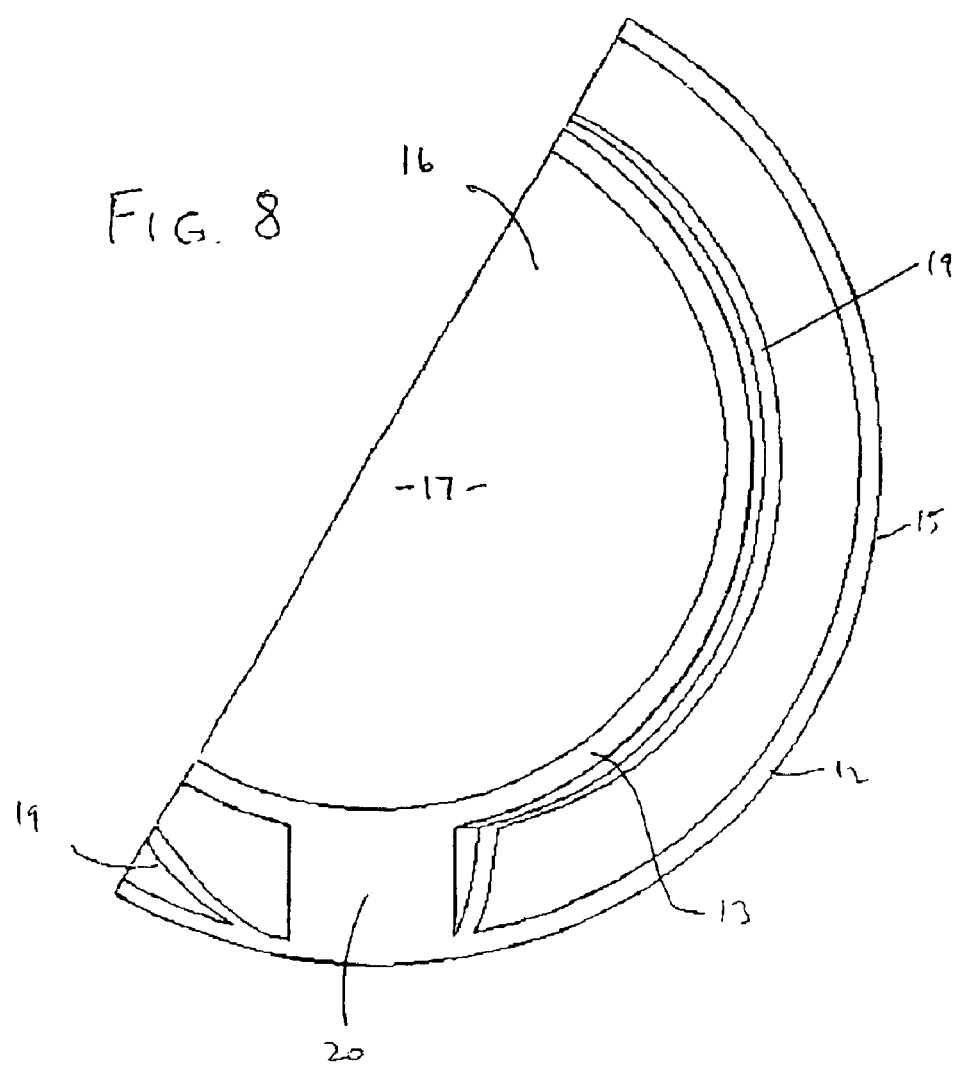

FIGS. 6 to 8 are further sectional views of the prosthesis of FIGS. 2 to 5.

DETAILED DESCRIPTION OF THE PREFERRED EMBODIMENT

Referring to FIG. 1 of the drawings, an acetabular prosthesis 1 made of cobalt-chrome comprises an outer cup-shaped portion 2 and an inner cup-shaped portion 3. Inner portion 3 is nested within but spaced from outer portion 2. Outer portion 2 has a substantially concave inner surface 4 and a substantially convex outer surface 5, while inner portion 3 has a substantially concave inner surface 6, which defines a frusto-conical cavity 7, and a substantially convex outer surface 8. Flexible connecting means in the form of thin vanes 9 connect the outer convex surface 8 of the inner portion 3 to the concave inner surface 4 of the outer portion 2. Such a prosthesis can be made by stereolithography. The flexibility in vanes 9 will be dependent upon the thickness thereof. Hence different flexibilities can be achieved by utilising different thicknesses of vanes 9 or by varying the thickness of vanes 9 along their length.

Cavity 7 is intended for receipt of a ceramic or plastics material liner (not shown) having in either case a part-spherical concave bearing surface for receipt of a ball head of a femoral implant. Alternatively it can be used to receive a metal insert (also not shown) having a polished part-spherical surface formed therein to act as a bearing surface for a ball head on a femoral implant.

As can be seen from the drawing, vanes 9 are petaloid in shape and are attached along curving spiral form paths to the outer surface 8 of inner portion 3 and to the inner surface 4 of outer portion 2.

Acetabular prosthesis 1 can alternatively be made from a suitable synthetic biocompatible material, such as a carbon fibre-reinforced resin material. The resin in such a material can be, for example, an epoxy resin. Such a material not only provides the prosthesis with sufficient strength but it also has sufficient resilience for vanes 9 to flex under extreme load.

The outer surface 5 of outer portion 2 can be provided with pores or with an adhesively bonded layer of hydroxyapatite with a view to encouraging bone ingrowth.

Due to the resilient nature of vanes 9, in the event of unusually high load forces later being imposed upon the patient's hip joint (for example, as a result of stumbling), the inner portion 3 can move slightly relative to outer portion 2 and so the acetabular prosthesis 1 can accept the resultant high stresses with a greatly reduced risk of damage to the patient's pelvic bones or of dislodgement of the prosthesis 1 such as by breakage of any cement joint between the prosthesis 1 and the patient's pelvis which helps to retain the prosthesis 1 in the bone.

In an alternative embodiment the empty spaces between inner portion 2 and outer portion 3 are filled with a resilient material such as silicone rubber.

A second acetabular prosthesis 11 is illustrated in FIGS. 2 to 8. This comprises an outer substantially hemispherical cup-shaped portion 12 and an inner substantially hemispherical cup-shaped portion 13 which is nested within but spaced from outer cup-shaped portion 12. Outer portion 12 has a substantially concave inner surface 14 and a substantially convex outer surface 15, while inner portion 13 has a substantially part spherical concave inner surface 16, which defines a cavity 17, and a substantially convex outer surface 18. Flexible connecting means in the form of three thin vanes 19 connect the outer convex surface 18 of the inner portion 13 to the concave inner surface 14 of the outer portion 12. Prosthesis 11 is typically constructed of cobalt-chrome or a titanium alloy and can be made by stereolithography. The flexibility in vanes 19 will be dependent upon the thickness thereof.

Cavity 17 is intended for receipt of a metal insert (not shown) having a polished part-spherical concave surface formed therein to act as a bearing surface for a ball head on a femoral implant. Alternatively the convex inner surface 16 can be polished so as to provide a bearing surface for a ball head on a femoral implant.

Vanes 19 are petaloid in shape and are attached along curving spiral form paths to the outer surface 18 of inner portion 13 and to the inner surface 14 of outer portion 12.

Acetabular prosthesis 11 can alternatively be made from a suitable synthetic biocompatible material, such as a carbon fibre-reinforced resin material. The resin in such a material can be an epoxy resin.

FIG. 4 is a sectional view corresponding to that of FIG. 2 of the prosthesis 11 taken on an oblique diametral plane passing through the centre of the opening to cavity 17.

The prosthesis 11 is illustrated in FIG. 5 in vertical cross section. This shows a spacer portion 20 which connects the inner portion 13 and the outer portion 12.

FIG. 6 is a further sectional view of the prosthesis 11 taken on a steeper oblique diametral plane than that of FIG. 4.

FIG. 7 is a further view of the prosthesis 11 which has been sectioned on the same plane as in FIG. 5 and also on a plane substantially orthogonal to that.

FIG. 8 is a still further view of the prosthesis 11 which has also been sectioned on two planes.

If desired the free spaces between the inner portion 13 and the outer portion 12 can be filled with a biocompatible resilient material such as a silicone rubber. Moreover the outer surface 15 can be coated with an adhesively bonded layer of hydroxyapatite, or it can be provided with pores, with a view to encouragement of bone ingrowth.

In use of the acetabular prosthesis 1 or 11, the surgeon will prepare the patient's hip for implantation in conventional manner. Then, after reaming out, if necessary, a socket of suitable size in the patient's pelvic bone, the prosthesis 1 or 11 can be implanted and secured in position with the aid of bone cement and, optionally, with the aid of screws passed through appropriate apertures (not shown) drilled through the outer portion 2 or 12. The surgical wound can then be closed in conventional fashion and the patient rehabilitated using conventional physiotherapy.

What is claimed is:

1. An acetabular prosthesis comprising:
   an outer portion having a substantially concave inner surface and a substantially convex outer surface;
   an inner portion within and spaced from the outer portion and having a substantially concave inner surface defining a cavity and a substantially convex outer surface; and
   flexible connecting means connecting the outer convex surface of the inner portion to the concave inner surface of the outer portion;
   the inner portion, outer portion and flexible connecting means being monolithically formed from a single type of material.

2. An acetabular prosthesis according to claim 1, wherein the flexible connecting means is made from a biocompatible material.

3. An acetabular prosthesis according to claim 2, wherein the flexible connecting means is made from a material selected from the group consisting of a titanium alloy, cobalt-chrome, and a carbon fibre reinforced plastics material.

4. An acetabular prosthesis according to claim 1, wherein the outer portion is made from a biocompatible material.

5. An acetabular prosthesis according to claim 1, wherein the outer portion is made from a material selected from the group consisting of a titanium alloy, cobalt-chrome, and a carbon fibre reinforced plastics material.

6. An acetabular prosthesis according claim 1, wherein the inner portion is made from a biocompatible material.

7. An acetabular prosthesis according to claim 6, wherein the inner portion is made from a material selected from the group consisting of a titanium alloy, cobalt-chrome, and a carbon fibre-reinforced plastics material.

8. An acetabular prosthesis according to claim 1, wherein the cavity is defined in part by a frusto-conical surface.

9. An acetabular prosthesis according to claim 1, wherein, the cavity is defined in part by a substantially part spherical concave inner surface.

10. An acetabular prosthesis according to claim 9, wherein the inner portion is made from material selected from the group consisting of a titanium alloy and cobalt-chrome and wherein the substantially concave inner surface thereof is substantially part spherical and is provided with a polished finish.

11. An acetabular prosthesis according to claim 1, wherein the flexible connecting means comprises plurality of petaloid vanes integrally formed with the inner and outer portions.

12. An acetabular prosthesis according to claim 11, wherein there are three petaloid vanes.

13. An acetabular prosthesis according to claim 11, wherein the vanes join the outer surface of the inner portion and the inner surface of the outer portion in each case along spiral paths.

14. An acetabular prosthesis according to claim 1, wherein at least a part of the space remaining between the inner portion and the outer portion is filled with a resilient material.

15. An acetabular prosthesis according to claim 14, wherein the resilient material comprises a silicone rubber.

16. An acetabular prosthesis according to claim 1, wherein at least a part of the substantially convex outer surface of the outer portion is porous.

17. An acetabular prosthesis according to claim 1, wherein at least a part of the substantially convex outer surface of the outer portion bears an adhesively bonded layer of hydroxyapatite.

18. An acetabular prosthesis comprising:
   an outer portion having a substantially concave inner surface and a substantially convex outer surface;
   an inner portion within and spaced from the outer portion and having a substantially concave inner surface defining a cavity and a substantially convex outer surface; and
   flexible connecting means connecting the outer convex surface of the inner portion to the concave inner surface of the outer portion, the flexible connecting means comprising a plurality of petaloid vanes which join the outer surface of the inner portion and the inner surface of the outer portion in each case along spiral paths;
   the inner portion, outer portion and plurality of petaloid vanes being monolithically formed from a single type of material.

19. An acetabular prosthesis comprising:
   an outer portion having a substantially concave inner surface and a substantially convex outer surface;
   an inner portion within and spaced from the outer portion and having a substantially concave inner surface defining a cavity and a substantially convex outer surface; and
   flexible connecting means connecting the outer convex surface of the inner portion to the concave inner surface of the outer portion, the flexible connecting means comprising three petaloid vanes integrally formed with the inner and outer portions.

* * * * *